(12) United States Patent
Benesh et al.

(10) Patent No.: US 7,196,100 B2
(45) Date of Patent: Mar. 27, 2007

(54) OPIOID RECEPTOR ANTAGONISTS

(75) Inventors: Dana Rae Benesh, Westfield, IN (US); Maria-Jesus Blanco-Pillado, Indianapolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 10/581,164

(22) PCT Filed: Dec. 6, 2004

(86) PCT No.: PCT/US2004/038227

§ 371 (c)(1),
(2), (4) Date: May 31, 2006

(87) PCT Pub. No.: WO2005/061442

PCT Pub. Date: Jul. 7, 2005

(65) Prior Publication Data

US 2007/0010558 A1    Jan. 11, 2007

(51) Int. Cl.
*A61K 31/445* (2006.01)
*A61K 31/165* (2006.01)
*A61K 31/44* (2006.01)
*A61K 31/435* (2006.01)
*C07D 211/68* (2006.01)

(52) U.S. Cl. .................. 514/318; 514/336; 514/619; 514/327; 514/346; 514/282.1; 546/193; 546/194; 546/221; 546/280.4; 546/291; 564/167

(58) Field of Classification Search ............... 514/318, 514/336, 327, 619, 350, 346; 546/193, 194, 546/221, 280.4, 291, 282.1; 564/167
See application file for complete search history.

(56) References Cited

U.S. PATENT DOCUMENTS

2005/0182040 A1    8/2005    Imazaki et al.

FOREIGN PATENT DOCUMENTS

| EP | 1 072 592 | 1/2001 |
|---|---|---|
| JP | 2004/002367 | 1/2004 |
| WO | WO 99/33806 | 7/1999 |
| WO | WO 01/46174 | 6/2001 |
| WO | WO 01/74806 | 10/2001 |
| WO | WO 02/48122 | 6/2002 |
| WO | WO 03/029233 | 4/2003 |
| WO | WO 2004/026305 | 4/2004 |
| WO | WO 2004/037800 | 5/2004 |
| WO | WO 2004/080968 | 9/2004 |
| WO | WO 2004/080996 | 9/2004 |

OTHER PUBLICATIONS

Hcaplus 136:325560.*

* cited by examiner

*Primary Examiner*—Bernard Dentz
*Assistant Examiner*—Binta Robinson
(74) *Attorney, Agent, or Firm*—John C. Demeter; Francis O. Ginah

(57) ABSTRACT

A compound of the formula (I) wherein the variables $X_1$ to $X_5$, $R^1$ to $R^7$ including $R^{3'}$, E, q, v, y, z, A and B are as described, or a pharmaceutically acceptable salt, solvate, enantiomer, racemate, diastereomer or mixtures thereof, useful for the treatment, prevention or amelioration of obesity and Related Diseases is disclosed (I)

$(NR^1R^2)_q$—$(CR^3R^{3'})_v$—$A$—$O$—$\underset{X_5=X_4}{\overset{X_1=X_2}{B}}$—$NR^6R^7$ with $(R^4)_y$, $(R^5)_z$, E

3 Claims, No Drawings

OPIOID RECEPTOR ANTAGONISTS

The present invention is in the field of medicinal chemistry. The invention relates specifically to compounds useful as opioid antagonists, methods of treatment, methods of using, and pharmaceutical compositions thereof.

BACKGROUND

Three types of opioid receptors, mu, kappa, and delta opioid receptors are generally reported. Recent evidence points to the interactions between receptor dimer combinations of mu, kappa and/or delta receptors (called heterodimers) as also contributing to opioid activity. Opioid receptors and their normal regulation or lack thereof, has been implicated in disease states including irritable bowel syndrome, nausea, vomiting, pruritic dermatoses, depression, smoking and alcohol addiction, sexual dysfunction, stroke and trauma in animals. Therefore it is not surprising that the ability to antagonistically bind opioid receptors has been shown to produce ameliorative, preventative and/or treatment effects in animals including humans afflicted with one or more of these disease states.

More recently, certain antagonists of the opioid receptors have been found to increase metabolic energy consumption, and reduction of weight in obese rats while maintaining muscle mass. These findings indicate that an effective opioid antagonist may be useful in preventing, treating and/or ameliorating the effect of obesity. Considering the percentage of the population that is obese in Western societies and the indirect costs associated with treating the effects and symptoms of obesity and Related Diseases, the importance of these findings cannot be overstated.

Though many opioid antagonists have been disclosed, the search continues for alternative and/or improved or more effective antagonists having an overall benefit to the patient with little or no major side effects. U.S. Pat. No. 4,891,379 disclosed phenylpiperidine opioid antagonists useful for the treatment of diabetes and obesity. In particular, U.S. Pat. No. 4,891,379 disclosed the compound LY 255582 represented by the structure:

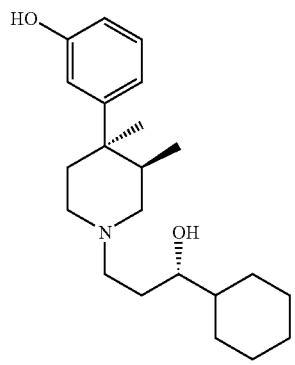

U.S. Pat. No. 4,191,771 also disclosed compounds useful as opioid antagonists. Also, bicyclic analogs of phenyl piperidine have been prepared and reported as opioid antagonists in Wentland, et al., Biorganic and Medicinal Chemistry Letters 11 (2001) 623–626; see also Wentland, et al., Bioorganic and Medicinal Chemistry Letters 11 (2001) 1717–1721. Finally, European Patent application number EP 1 072592A2 filed May 18, 2000, discloses phenylpiperidine compounds of formula 1

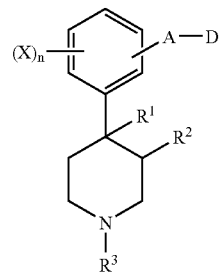

wherein A, D, $R^1$, $R^2$, $R^3$, X, and n have meanings given in the description, which are useful in the prophylaxis and in the treatment of diseases mediated by opioid receptors such as pruritus.

U.S. Pat. No. 6,140,352 and related patents disclose the compound of formula Formula 1

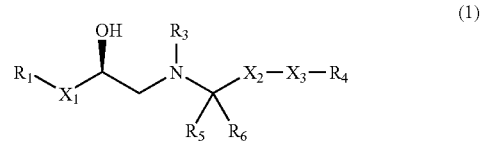

wherein the variables $X_1$, $X_2$, $X_3$ $R_1$, $R_3$, $R^4$, $R_5$ and $R_6$ are as described therein, as agonists of the beta adrenergic receptor useful for the treatment of diabetes and obesity.

Regardless of these and other disclosures of compounds useful as opioid receptor antagonists, or useful for the treatment of obesity, and/or diabetes by other mechanisms, there remains an unmet medical need for a safe, effective and/or alternate treatment or prophylaxis of diseases associated with opioid receptors, particularly obesity and Related Diseases.

SUMMARY OF THE INVENTION

The present invention provides a compound of the formula I

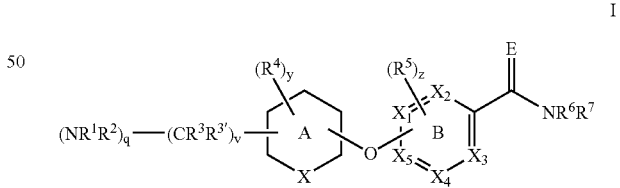

wherein
each of $X_1$, $X_2$, $X_3$, $X_4$, and $X_5$ is C, CH, or N; provided that ring B has no more than 2 nitrogen atoms;
X is NH or $CH_2$, so that ring A is cyclohexyl, cyclohexenyl, or piperidinyl;
E is NH or O;
v is 0, 1, 2, or 3;
q is 0 or 1, provided that when the A-ring is cyclohexyl or cyclohexenyl q is 1 and provided that v and q are not simultaneously 0;

R¹ and R² are independently selected from hydrogen, $C_1$–$C_8$ alkyl, $C_2$–$C_8$ alkenyl, $C_2$–$C_8$ alkynyl, aryl, $C_3$–$C_8$ cycloalkyl, $C_1$–$C_{10}$ alkylaryl, heterocyclyl, $C_1$–$C_{10}$ alkylheterocyclic, —$C_1$–$C_8$ alkylC(O)$C_1$–$C_8$ alkyl, —(CH$_2$)$_n$(CO)$C_3$–$C_8$ cycloalkyl-, —$C_2$–$C_8$ alkylCH(OH)aryl, —, —CO(O)$C_1$–$C_8$alkyl, —SO$_2$$C_1$–$C_8$alkyl, —SO$_2$$C_1$–$C_{10}$ alkylaryl, —SO$_2$$C_1$–$C_8$ alkylheterocyclic, —$C_1$–$C_8$ alkylcycloalkyl, —(CH$_2$)$_n$C(O)OR⁸, —(CH$_2$)$_n$C(O)R⁸, —(CH$_2$)$_m$C(O)NR⁸R⁸, and —(CH$_2$)$_m$NSO$_2$R⁸; wherein each of the alkyl alkenyl, cycloalkyl, heterocyclic, and aryl groups are optionally substituted with one to five groups independently selected from halo, $C_1$–$C_8$ haloalkyl, $C_1$–$C_8$ thioalkyl, $C_1$–$C_8$ alkyl, $C_2$–$C_8$ alkenyl, aryl, —$C_1$–$C_8$ alkylaryl, —C(O)$C_1$–$C_8$ alkyl, —SO$_2$$C_1$–$C_8$ alkyl, —SO$_2$$C_1$–$C_8$ alkylaryl, —$C_1$–$C_8$ alkylaryl; and wherein R¹ and R² may optionally combine with each other to form a 4, 5, 6, or 7-membered nitrogen-containing heterocycle which nitrogen-containing heterocycle may further have substituents selected from the group consisting of amino, $C_1$–$C_8$ alkyl, $C_2$–$C_8$ alkenyl, $C_2$–$C_8$ alkynyl, aryl, $C_1$–$C_8$ alkylaryl, —C(O)$C_1$–$C_8$ alkyl, —CO(O)$C_1$–$C_8$ alkyl, halo, oxo, $C_1$–$C_8$ haloalkyl;

R³ and R³' are each independently selected from hydrogen, $C_1$–$C_8$ alkyl, $C_2$–$C_8$ alkenyl, $C_2$–$C_8$ alkynyl, aryl, —$C_1$–$C_8$ alkylcycloalkyl, or —$C_1$–$C_8$ alkylaryl; $C_1$–$C_8$ alkylheterocyclic;

or R³ and R³' combine to form a $C_3$–$C_8$ cycloalkyl, $C_4$–$C_8$ cycloalkenyl, or $C_5$–$C_{10}$ heterocyclic;

R⁴ and R⁵ are each independently selected from hydrogen, $C_1$–$C_8$ alkyl, $C_2$–$C_8$ alkenyl, —$C_2$–$C_8$ alkynyl, —$C_1$–$C_8$ alkoxyalkyl, $C_1$–$C_8$ thioalkyl, halo, $C_1$–$C_8$ haloalkyl, —$C_1$–$C_8$ alkoxyhaloalkyl, aryl, —$C_1$–$C_8$ alkylaryl, —C(O)$C_1$–$C_8$ alkyl, or —C(O)OC$_1$–$C_8$ alkyl, —$C_1$–$C_8$ alkylamino, —$C_1$–$C_8$ alkylcycloalkyl, —(CH$_2$)$_m$C(O)$C_1$–$C_8$ alkyl, and (CH$_2$)$_n$NR⁸R⁸, wherein each R⁴ or R⁵ is attached to its respective ring only at carbon atoms, and wherein y is 0, 1, 2, or 3; and wherein z is 0, 1, 2, or 3;

R⁶ and R⁷ are each independently selected from hydrogen, $C_1$–$C_8$ alkyl, $C_2$–$C_8$ alkenyl, $C_2$–$C_8$ alkynyl, —C(O)$C_1$–$C_8$ alkyl, hydroxy, $C_1$–$C_8$ alkoxy, —SO$_2$$C_1$–$C_8$ alkyl, SO$_2$$C_1$–$C_8$ alkylaryl, —SO$_2$$C_1$–$C_8$ alkylheterocyclic, aryl, —$C_1$–$C_8$ alkylaryl, $C_3$–$C_7$ cycloalkyl, —$C_1$–$C_6$ alkylcycloalkyl, —(CH$_2$)$_n$C(O)R⁸, —(CH$_2$)$_m$C(O)NR⁸R⁸, and —(CH$_2$)$_m$NSO$_2$R⁸; wherein each of the alkyl, alkenyl, and aryl groups are optionally substituted with one to five groups independently selected from $C_1$–$C_8$ alkyl, $C_2$–$C_8$ alkenyl, aryl, and $C_1$–$C_8$ alkylaryl; and wherein R⁶ and R⁷ may independently combine with each other to form a 4, 5, 6, or 7-membered nitrogen-containing heterocycle which nitrogen-containing heterocycle may optionally have substituents selected from the group consisting of oxo, $C_1$–$C_8$ alkyl, $C_2$–$C_8$ alkenyl, $C_2$–$C_8$ alkynyl, aryl, —$C_1$–$C_8$ alkylaryl, —C(O)$C_1$–$C_8$ alkyl, —CO(O)$C_1$–$C_8$ alkyl, hydroxy, $C_1$–$C_8$ alkoxy, —$C_1$–$C_8$ alkylamine, amino, halo, and haloalkyl;

R⁸ is hydrogen, $C_1$–$C_8$ alkyl, $C_2$–$C_8$ alkenyl, $C_1$–$C_8$ alkylaryl, —C(O)$C_1$–$C_8$ alkyl or —C(O)OC$_1$–$C_8$ alkyl; and wherein n is 0, 1, 2, 3 or 4 and m is 1, 2, or 3;

or a pharmaceutically acceptable salt, solvate, enantiomer, racemate, diastereomer or mixture of diastereomers thereof.

The present invention also provides a pharmaceutical formulation comprising a compound of formula I in association with a carrier, diluent and/or excipient.

The present invention also relates to a method for the treatment and/or prophylaxis of obesity and Related Diseases including eating disorders (bulimia, anorexia nervosa, etc.), diabetes, diabetic complications, diabetic retinopathy, sexual/reproductive disorders, depression related to obesity, anxiety related to obesity, epileptic seizure, hypertension, cerebral hemorrhage, congestive heart failure, sleeping disorders, atherosclerosis, stroke, metabolic diseases and symptoms thereof, hyperlipidemia, hypertriglycemia, hyperglycemia, hyperlipoproteinemia, substance abuse, drug overdose, compulsive behavior disorders (such as paw licking in dog), and addictive behaviors such as for example, gambling, and alcoholism, comprising administering a therapeutically effective amount of a compound of formula I or a pharmaceutically acceptable salt, solvate, enantiomer, racemate, diastereomer or mixture of diastereomers thereof.

The present invention provides a compound of formula I useful for the manufacture of a medicament for the treatment, prevention and/or amelioration of symptoms associated with obesity and Related Diseases.

In another embodiment, the present invention provides a compound of formula I or a pharmaceutically acceptable salt, solvate, enantiomer, racemate, diastereomer or mixtures thereof, useful as an appetite suppressant.

In another embodiment, the present invention provides a method of achieving weight loss while maintaining or minimizing the loss of lean muscle mass, comprising administering a compound of formula I or a pharmaceutically acceptable salt, solvate, enantiomer, racemate, diastereomer or mixtures thereof, to a patient in need thereof.

In yet another embodiment, the present invention provides a compound of formula I or a pharmaceutically acceptable salt, solvate, enantiomer, racemate, diastereomer or mixture thereof, to a patient in need thereof in combination with other effective therapy for the treatment of obesity and related disorders.

DETAILED DESCRIPTION OF THE INVENTION

As used herein the term "obesity" has its commonly understood meaning such as "excessively fat" and includes the clinical designation of being obese as defined in and by the medical literature and brochures of support or public health organizations. For example, *Dorland's Illustrated Medical Dictionary* (29$^{th}$ edition, W. B. Saunders Company, Philadelphia USA.) defines obesity as "an increase in body-weight beyond the limitation of skeletal and physical requirements, as the result of an excessive accumulation of fat in the body." Because the decision of suitability administration of a compound(s) of the present invention to a patient is to be made by a qualified physician or qualified caregiver, the patient is inherently deemed suitable or obese by the administering caregiver.

As used herein, the term "patient" includes human and non-human animals such as companion animals (dogs and cats) and livestock animals.

The preferred patient of treatment, amelioration and/or prevention of obesity and Related Diseases are human.

The terms "treating" and "treat", as used herein, include their generally accepted meanings, i.e., preventing, prohibiting, restraining, alleviating, ameliorating, slowing, stopping, or reversing the progression or severity of a pathological condition, or sequela thereof, described herein.

The terms "ameliorating" "preventing", "prevention of", "prophylaxis", "prophylactic" and "prevent" are used herein interchangeably and refer to reducing the severity of the symptoms associated with obesity and Related Diseases in a patient afflicted with same or reducing the likelihood that the recipient of a compound of formula I will incur or develop any of the pathological conditions, or sequela thereof, described herein.

As used herein, the term "effective amount" is synonymous with "effective dose" and means an amount of a compound of formula I that is sufficient in one or more administrations for preventing, ameliorating or treating a condition, or detrimental effect thereof, herein described, or an amount of a compound of formula I that is sufficient for antagonizing the opioid receptors to achieve the desired outcome within the purview of the invention.

The term "pharmaceutically acceptable" is used herein as an adjective and means substantially non-deleterious to the recipient patient.

The term "Active Ingredient" as used herein means a compound of formula I or a combination of compounds of formula I or a combination of a compound of formula I and a co-antagonist of the opioid receptor or a combination of a compound of formula I in addition to other effective anti-obesity, weight loss or anti-diabetic agent(s).

The term "formulation", as in pharmaceutical formulation, or "pharmaceutical composition" is intended to encompass a product comprising the Active Ingredient (as defined supra), and the inert ingredient(s) that make up the carrier, or other components of the drug as administered, as well as any product which results, directly or indirectly, from combination, complexation or aggregation of any two or more of the Active ingredients, or from dissociation of one or more of the Active ingredients. Accordingly, the pharmaceutical formulations of the present invention encompass any effective composition made by admixing a compound of the present invention and a pharmaceutical carrier. The pharmaceutical formulations of the present invention also encompass a compound of the formula I and a pharmaceutically acceptable co-antagonist of opioid receptors or other effective therapy useful for the treatment and/or prevention of obesity or Related Diseases.

The term "Related Diseases" as used herein refers to such symptoms, diseases or conditions caused by, exacerbated by, induced by or adjunct to the condition of being obese. Such diseases, conditions and/or symptoms include but are not limited to eating disorders (bulimia, anorexia nervosa, etc.), diabetes, diabetic complications, diabetic retinopathy, sexual/reproductive disorders, obesity related depression, obesity related anxiety, epileptic seizure, hypertension, cerebral hemorrhage, congestive heart failure, sleeping disorders, atherosclerosis, stroke, metabolic diseases and symptoms thereof, hyperlipidemia, hypertriglycemia, hyperglycemia, and hyperlipoproteinemia. As used herein the terms obesity related depression and obesity related anxiety are conditions of depression and anxiety respectively, that are symptomatic of certain obese patients and possibly brought on by the awareness or self-consciousness of the condition of being obese and possibly coupled with the real or perceived notion of acceptance or rejection by the certain individual, individuals or the public at large. Obesity related depression or anxiety may generally be alleviated or treated adjunctively with the underlying condition of being obese or overweight and/or prevented by administration of a compound of formula I.

The term "suitable solvent" refers to any solvent, or mixture of solvents, inert to the ongoing reaction that sufficiently solubilizes the reactants to afford a medium within which to effect the desired reaction.

The term "mutual solvent" means a solvent that is used to dissolve sufficiently, two or more components of a reaction or mixture separately prior to reaction or mixing, that is a solvent common to more than one reagents or components of a mixture.

The term "nitrogen containing heterocycle" refers to a aromatic or non-aromatic, monocyclic or bicyclic ring system which is a 4, 5, 6, or 7-member ring containing 1, 2 or 3 nitrogen atoms in addition to the carbon atoms completing the ring size, or a combination of 1 nitrogen atom and 1, or 2 atoms selected from oxygen, and sulfur in addition to the appropriate number of carbon atoms completing the ring size. A nitrogen containing heterocycle as used here may have 0, 1, 2 or 3 double bonds.

The term "$C_1$–$C_8$ alkyl" or $C_{1-8}$ alkyl" refers to and includes all groups, structural isomers and/or homologues of alkyl groups having from 1 to 8 carbon atoms. When the term $C_1$–$C_8$ alkyl precedes or prefixes another group, the term $C_1$–$C_8$ alkyl, only limits the number of carbon atoms in the alkyl component. For example $C_1$–$C_8$ alkyaryl means an aryl group having a $C_1$–$C_8$ alkyl group substituent such that the number of carbon atoms in the group $C_1$–$C_8$ alkylaryl is effectively the number of carbon atoms in the aryl group plus the number of carbon atoms in the $C_1$–$C_8$ alkyl group. Similarly, the term "$C_1$–$C_8$ alkylcycloalkyl" refers to a cycloalkane group having a $C_1$–$C_8$ alkyl substituent, and wherein the entire group $C_1$–$C_8$ alkylcycloalkane may itself be a substituent attached at either the alkyl group or the cycloalkyl group to a substrate. The definition and usage applies equally to other homologues of $C_1$–$C_8$ such as for example, $C_1$–$C_7$, $C_1$–$C_6$ etc. In general, and where necessary a dash (–) has been placed next to certain groups to indicate the point of attachment for clarity. Nevertheless, the absence of a dash does not otherwise negate the position obvious postion(s) of attachment known to one of skill in the art.

The term "cycloalkane" or "cycloalkyl" means cycloalkanes having from 3 to 8 carbon atoms i.e. from cyclopropane to cyclooctane.

The term "hal" or "halo" as used herein refers to a halogen including fluorine, chlorine, bromine or iodine.

The term "haloalkane" or "haloalkyl" means haloalkanes having from 1 to 8 carbon atoms, and from 1 to 3 halogen atoms as allowed by valency considerations. Examples include chloroethyl, trifluoromethyl, 2-chloropropyl, etc.

As used herein the terms "alkenyl" refers to straight or branched carbon atoms having 1 or 2 carbon-carbon double bonds.

As used herein the terms "alkynyl" refers to straight or branched carbon atoms having 1 or 2 carbon-carbon triple bonds.

As used herein the term "alkoxy" refers to the group "O-alkyl" wherein alkyl is as defined previously.

The term "aryl" as used herein refers to compounds or groups having the Huckel 4n+2 pi electron arrangement and includes for example, phenyl, benzyl, naphthyl, tetrahydronaphthyl, benzothiophene, etc, but excludes carbazoles and other fused tricyclic ring structures.

As used herein the term "aroxy" or "aryloxy" refers to the group "O-aryl" wherein aryl is as defined previously.

As used herein the term "fused bicyclic" means a fused cycloalkane ring system wherein each ring has from 4 to 8 carbon atoms (i.e. $C_8$–$C_{16}$ fusedbicyclic) and the fused ring system has from 0 to 3 bridgehead carbon atoms. One or both of the fused rings may contain zero or one double bond. Examples of fused bicyclics include but are not limited to bicyclo[2,2,1]heptyl, bicyclo[2,2,1]heptenyl.

As used herein the term "heterocyclic" or "heterocyclyl" or "heterocycle" are used interchangeably and has its usual meaning and includes mono, bi or tricyclic or spirocyclic heterocyclic groups unless otherwise specified. Heterocycles as used herein may contain 1, 2, or 3 heteroatoms selected independently from nitrogen, oxygen or sulfur, unless otherwise specified. Examples of heterocylclic groups applicable to the present invention include but are not limited to pyranyl, piparazinyl, pyrrolidinyl, azapanyl, azaflorenyl, isoquinolinyl, indolinyl, thiophenyl, benzothiophenyl, oxazolyl, morpholinyl, thiomorpholinyl, and piperidinyl. Each of the heterocyclic groups may be mono or di substituted or as specified with substituents such as alkyl, cycloalkyl, aryl, among others as defined. Furthermore, substitution may be at the 1-position or heteroatom as in piperazine, pyrrolidine or at a carbon atom or both.

As used herein, the term "protecting group" refers to a group useful for masking reactive sites in a molecule to enhance the reactivity of another group or allow reaction at another desired site or sites following which the protecting group may be removed. Protecting groups are usually used to protect or mask groups including but not limited to —OH, —NH, and —COOH. Suitable protecting groups are known to one of skill in the art and are described in Protecting groups in Organic Synthesis, $3^{rd}$ edition, Greene, T. W.; Wuts, P. G. M. Eds., John Wiley and Sons, New York, 1999.

As used herein, the term "solvate" is a form of the compound of the invention wherein a crystal or crystals of a compound of the invention have been formed from a stoichiometric or non-stoichiometric amount of the compound of formula I and a solvent. Typical solvating solvents include for example, water, methanol, ethanol, acetone and dimethylformamide.

In those instances where a compound of the invention possesses acidic or basic functional groups, various salts may be formed which are more water soluble and/or more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion-exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," J. Phar. Sci., 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, clavulanate, citrate, chloride, edetate, edisylate, estolate, esylate, fluoride, fumarate, gluceptate, gluconate, glutamate, glycolylarsanilate, hexylresorcinate, hydrochloride, hydroxynaphthoate, hydroiodide, isothionate, lactate, lactobionate, laurate, maleate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate. Preferred salts for the purpose of the invention include the hydrochloride salt, the hydrobromide salt, the bisulfate salt, the methane sulfonic acid salt, the p-toluenesulfonic acid salt, bitartrate, the acetate and the citrate salt.

A compound of the invention as illustrated by formula I may occur as any one of its positional isomers, stereochemical isomers or regio-isomers, all of which are objects of the invention. Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of enantiomers or cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound i.e. a chiral resolving agent. This changes the racemic form into a mixture of stereoisomers and diastereomers, because they have different melting points, different boiling points, and different solubilities and can be separated by conventional means, such as crystallization.

PCT international application WO 02/078693 A2 published Oct. 10, 2002 discloses compounds of the formula

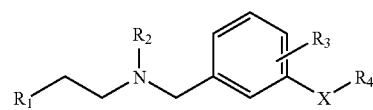

wherein $R_1$, $R_2$, $R_3$, $R_4$ and X are as described therein, as antagonists of the 5-$HT_6$ receptor for the treatment of disorders including cognitive disorders, age related disorders, mood disorders, psychosis, etc. The compounds of the present invention however, are useful for the treatment and/or prevention of obesity and Related Diseases. The compounds of the present invention have also shown inhibition of orexigenic effects, and are thus useful as appetite suppressants either as a single therapy or as combination therapy in conjunction with exercise and other effective appetite suppressing or weight loss medications.

The efficacy of certain compounds of the present invention have been demonstrated by their activity or potency in several biological models including a binding scintillation proximity assay (SPA) and functional GTP-gamma-S assay).

Preferred Embodiments of the Invention

A compound of formula I preferably exists as the free base or a pharmaceutically acceptable salt. More preferred is the hydrochloride salt, the bisulfate salt, mesylate or the oxalic acid salt of the compound of formula I.

Preferred embodiments of the compound of formula I include the substructures Ia, Ib Ic and Id as shown below:

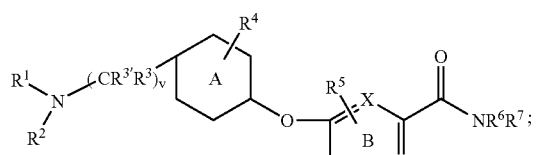

(Ia)

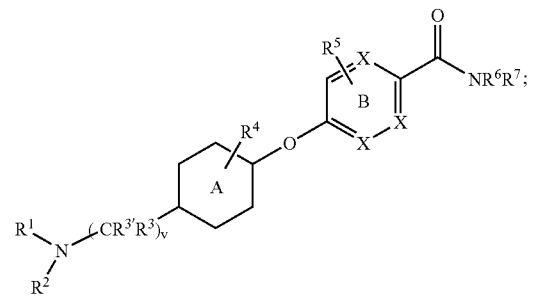

(Ib)

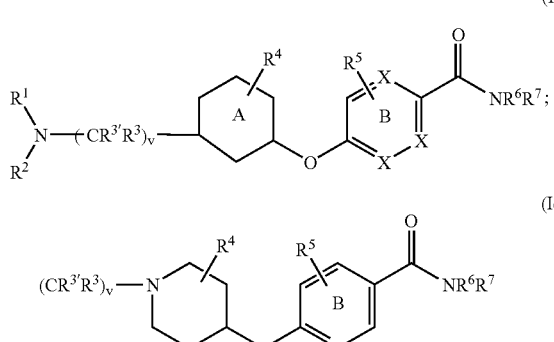

(Ic)

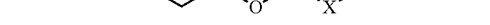

(Id)

For the Groups R¹ and R²

Preferred $R^1$ and $R^2$ groups are independently selected from the group consisting of hydrogen, methyl, ethyl, propyl, pentyl, phenyl, naphthyl, benzothiophene, and isopropyl.

Also preferred are $R^1$ and $R^2$ groups independently selected from the group consisting of methyl, ethyl, propyl, isopropyl, phenyl,

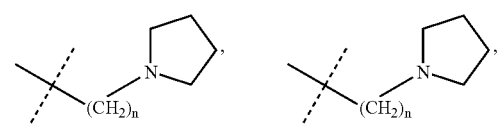

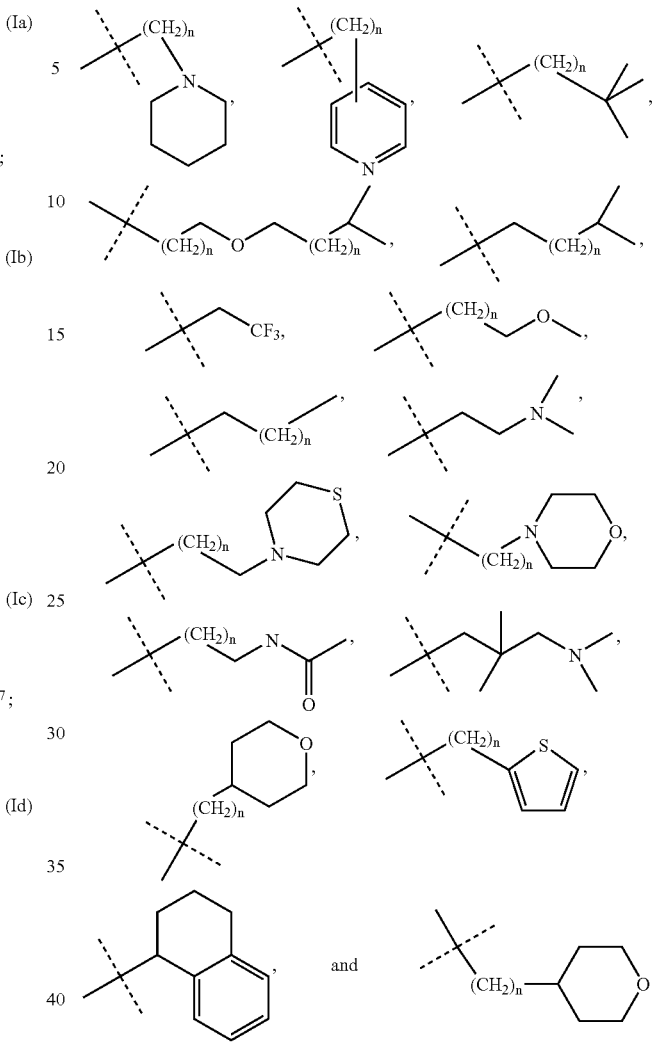

-continued each of which is optionally substituted with a group selected from the group consisting of halogen, $C_1$–$C_8$ alkyl, $C_1$–$C_8$ haloalkyl, $C_1$–$C_8$ thioalkyl, $C_1$–$C_8$ alkylamino, phenyl, $C_1$–$C_8$ alkylsubstituted phenyl, $C_4$–$C_8$ heterocycle or —$C_1$–$C_4$ alkylheterocycle; or combine with a group selected from $C_1$–$C_8$ alkyl, halogen, $C_1$–$C_8$ haloalkyl, $C_1$–$C_8$ thioalkyl, $C_1$–$C_8$ alkylamino, phenyl, $C_1$–$C_8$ alkylsubstituted phenyl, $C_4$–$C_8$ heterocycle or $C_1$–$C_4$ alkyl heterocycle to form a substituted or unsubstituted bicycle or tricycle, and wherein n is preferably 1, 2, or 3.

Also preferred are $R^1$ and $R^2$ groups that combine with each other or with 1 or 2 atoms adjacent to the nitrogen atom to form a group selected from the group consisting of

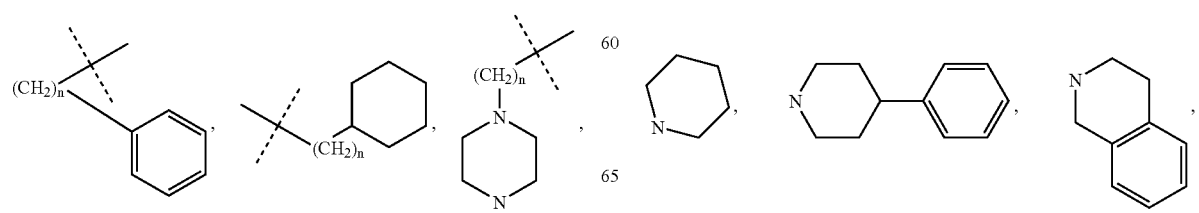

-continued

[chemical structures]

each of which is optionally substituted with a group selected from the group consisting of halogen, amino, $C_1$–$C_8$ alkyl, $C_1$–$C_8$ haloalkyl, $C_1$–$C_8$ thioalkyl, —$C_1$–$C_8$ alkylamino, phenyl, $C_1$–$C_8$ alkylsubstituted phenyl, $C_4$–$C_8$ heterocycle or —$C_1$–$C_4$ alkylheterocycle.

Preferred $R^3$ and $R^{3'}$ Groups

A preferred $R^3$ is hydrogen. A preferred $R^{3'}$ group is selected from hydrogen, methyl, ethyl, propyl, isopropyl, butyl, isobutyl, phenyl and benzyl.

Preferred $R^4$ Groups

A preferred $R^4$ group is selected from the group consisting of hydrogen, halo, $C_1$–$C_5$ alkyl, $C_1$–$C_5$ haloalkyl, $C_1$–$C_5$ alkoxy, —$C_1$–$C_5$ alkylamino, —N($C_1$–$C_5$ alkyl)$_2$, —NHC$_1$–$C_5$ alkyl, —$C_1$–$C_5$ alkylN($C_1$–$C_5$ alkyl)$_2$, —$C_1$–$C_5$ alkylNHC$_1$–$C_5$ alkyl, phenyl, –$C_1$–$C_5$ alkylphenyl, —$C_1$–$C_5$ alkylcycloalkyl, and $C_1$–$C_5$ thioalkyl. More preferred is a $R^4$ group selected from the group consisting of hydrogen, methyl, ethyl, isopropyl, chloro, fluoro, trifluoromethyl, methoxy, ethoxy, thiomethyl, phenyl, and benzyl. Most preferred is an $R^4$ group selected from the group consisting of hydrogen, methyl, ethyl, isopropyl, fluoro, chloro, trifluoromethyl, methoxy, ethoxy, propoxy, isopropoxy, and benzyl.

Though the groups $R^4$ and a $R^5$ may exist as multiple substituents on their respective ring substrates, a preferred embodiment of the invention involves compounds wherein each of $R^4$, and $R^5$ are independently singly or doubly substituted on their respective ring substrates.

Preferred $R^5$ Groups

A preferred $R^5$ group is selected from the group consisting of hydrogen, halo, $C_1$–$C_5$ alkyl, $C_1$–$C_5$ haloalkyl, $C_1$–$C_5$ alkoxy, —$C_1$–$C_5$ alkylamino, —N($C_1$–$C_5$ alkyl)$_2$,—NHC$_1$–$C_5$ alkyl, —$C_1$–$C_5$ alkylN($C_1$–$C_5$ alkyl)$_2$, —$C_1$–$C_5$ alkylNHC$_1$–$C_5$ alkyl, phenyl, —$C_1$–$C_5$ alkylphenyl, —$C_1$–$C_5$ alkylcycloalkyl, and $C_1$–$C_5$ thioalkyl. More preferred is an $R^5$ group selected from the group consisting of hydrogen, methyl, ethyl, isopropyl, chloro, fluoro, trifluoromethyl, methoxy, ethoxy, thiomethyl, phenyl, and benzyl. A most preferred $R^5$ group is selected from the group consisting of hydrogen, methyl, ethyl, isopopropyl, fluoro, chloro, trifluoromethyl, methoxy, ethoxy, trifluoromethoxy, and benzyl.

Preferred $R^6$ and $R^7$ Groups

Preferred are $R^6$ and $R^7$ groups independently selected from the group consisting of hydrogen, methyl, ethyl, propyl, pentyl, isopropyl, phenyl and benzyl.

Also preferred are compounds of formula I wherein $R^6$ and $R^7$ independently combine with each other, and with the nitrogen atom to which they are attached or with 1, or 2 atoms adjacent to the nitrogen atom to form a 4, 5, 6, or 7-membered nitrogen containing heterocycle which nitrogen containing heterocycle may optionally have substituents selected from the group consisting of oxo, amino, $C_1$–$C_8$ alkyl, $C_2$–$C_8$ alkenyl, $C_2$–$C_8$ alkynyl, phenyl, —$C_1$–$C_8$ alkylaryl, —C(O)$C_1$–$C_8$ alkyl, —CO(O)$C_1$–$C_8$ alkyl, hydroxy, $C_1$–$C_8$ alkoxy, halo, and haloalkyl.

Preferred Values for q q is preferably 0 when the A-ring is piperidinyl. P is preferably 1 when the A-ring is cyclohexyl.

Preferred E Group

A most preferred E group is an oxygen atom (O).

Preferred A-Ring

A preferred A-ring is a cylohexyl or piperidinyl. Most preferred A ring is cyclohexyl.

Preferred B-Ring

A preferred B-ring is a phenyl ring, a pyrazine ring, a pyrimidine ring or a pyridine ring. Most preferred B ring is a phenyl, pyrazine or pyridine ring.

Preferred Values for v, n and m

A preferred value for v is 0, 1, or 2.

A preferred value for n is 1, 2 or 3.

A preferred value for m is 1 or 2.

A preferred compound according to the present invention is a compound selected from the group consisting of:

±6-{4-[2-(tetrahydro-pyran-4-yl)-ethylamino]-cyclohexyloxy}-nicotinamide,

[chemical structure]

±6-[4-(3-Methyl-butylamino)-cyclohexyloxy]-nicotinamide,

[chemical structure]

±6-[4-(2-Thiophen-2-yl-ethylamino)-cyclohexyloxy]-nicotinamide

[chemical structure]

±4-[4-(3-Phenyl-propylamino)-cyclohexyloxy]-benzamide

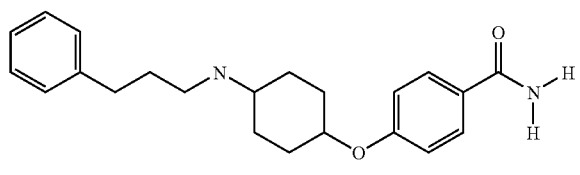

Trans-6-(4-Benzylamine-cyclohexyloxy)-nicotinamide,

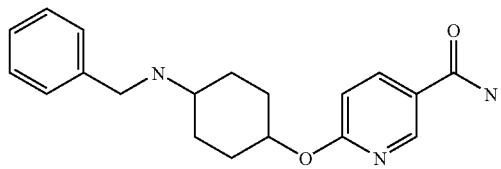

6-(1-Pyridin-2-ylmethyl-piperidin-4-yloxy)-nicotinamide

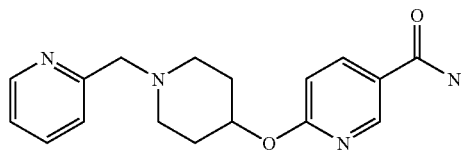

6-(1-Cycloproplymethyl-piperidin-4-yloxy)-nicotinamide

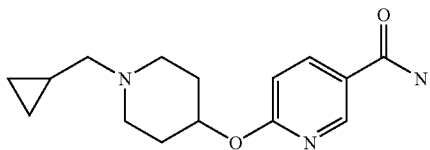

6-[1-(1H-Indol-2-ylmethyl)-piperidin-4-yloxy]-nicotinamide

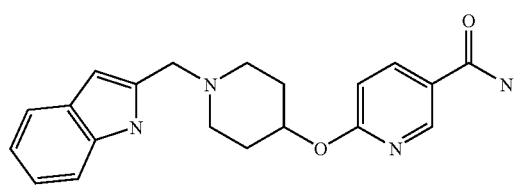

4-(1-Benzyl-piperidin-4-yloxy)-benzamide,

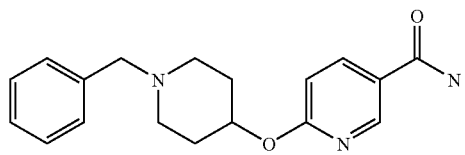

4-[1-(3-Phenyl-propyl)-piperidin-4-yloxy]-benzamide

and a pharmaceutically acceptable salt, solvate, enantiomer, diastereomer or a diastereomeric mixture thereof.

Preparing Compounds of the Invention

A typical protocol for the preparation of compounds of the invention and intermediates thereof wherein the A-ring is an optionally substituted cyclohexyl group is depicted in Scheme 1 below.

Scheme 1

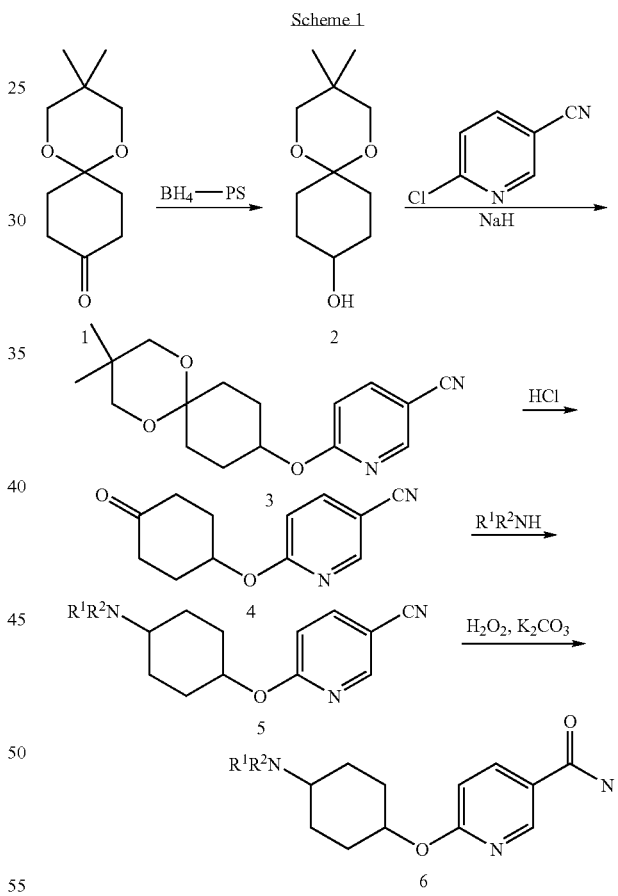

According to Scheme 1, the starting material 3,3-Dimethyl-1,5-dioxa-spiro[5.5]undecanone (1) and analogs thereof is reduced to the corresponding alcohol 3,3-Dimethyl-1,5-dioxa-spiro[5.5]undecan-9-ol (2) by reaction with polymer supported borohydride in a methanolic solvent. One of skill in the art is aware that other reducing agents and modes of reduction (e.g. without polymer support) may be utilized to afford the compound 2 and analogs thereof. The ketone 1 and analogs thereof may be purchased from Chemical distributors such as for example, Aldrich Chemical Co, Milawaukee, USA. The compound 3,3-Dimethyl-1,5-dioxaspiro[5.5]undecan-9-ol (2) is then coupled with halo nicotinonitrile or halobenzonitrile or other B-ring source to afford the oxygen linked compound 3 or analog thereof. For example, optionally substituted 4-chloronicotinonitrile is reacted with compound 2 to afford the oxygen-linked compound 3 under basic conditions. Basic conditions include the use of bases selected from inorganic and organic bases. Examples of useful inorganic bases include but are not limited to potassium carbonate, sodium hydride, sodium carbonate, sodium hydroxide, potassium hydroxide, calcium carbonate and cesium carbonate. Examples of organic bases include but are not limited to potassium hexamethyl disilazide, n-butyl lithium, hexamethylphophorous triamide, (HMPT), and the like. The basic conditions are complemented by the presence of a solvent, preferably an organic solvent. Preferred organic solvents include protic solvents or polar aprotic solvents. Most preferred solvents include dimethylformamide, methanol, dimethylacetamide (DMA), dimethylsulfoxide. A most preferred basic reaction condition involves the use of potassium carbonate in dimethylacetamide at temperatures of about 60 to 100° C. The protecting group (dimethylacetal group) of compound 3 is removed by reaction with an acidic group such as for example, hydrochloric acid to afford the compound 4. The compound 4 is reductively aminated with a desired amine to afford the amino compound 5, which is a compound of the invention. The reductive amination may be performed in two steps or a single step depending on the stability of the intermediate imine intermediate. Typically, compound 4 is reacted with a primary or secondary amine (primary amine shown) in methanol as solvent. Molecular sieves may be added to enhance the efficiency of the imine formation. In a second step the reducing agent, typically, sodium borohydride or other hydride reducing agent is added to the reaction mixture. The progress of the reaction may be monitored by TLC, HPLC, LC-MS or other analytical technique known to one of skill in the art to determine the substantial completion of each step and timing for the addition of the next reagent. The resulting amino nitrile compound 5 is hydrolyzed at the cyano group to afford the primary amide 6. Nitrile hydrolysis is preferably accomplished by reaction with hydrogen peroxide and an inorganic base such as sodium carbonate and preferably under pressure. A suitable solvent for accomplishing the above nitrile hydrolysis is DMSO or DMF.

Analogues of compounds 3 and 5 having one or more substituent R groups may be prepared by using appropriately substituted starting materials or by inter-conversion of substituent functionality. For example an initial optional substituent group on the A or B ring may be protected and deprotected appropriately to achieve the desired end substituent R. Alternatively an initial substituent may be converted by known 1, 2 or 3 step reactions to other desired final substituents.

An alternate protocol illustrated in Scheme 2 shows the use of the benzamide as the source of ring B.

Scheme 2

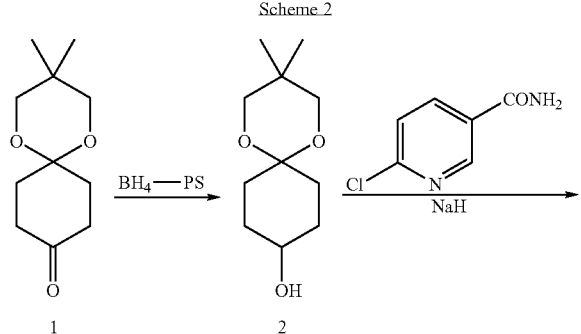

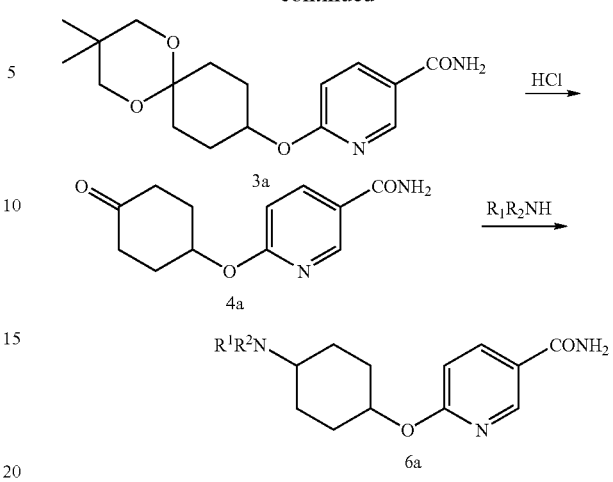

The use of the amide starting material is particularly preferred for compounds of the invention where the B-ring is pyridinyl, pyridazinyl, pyrazinyl or pyrimidinyl group. The carboxamide or heterocyclic amide may be introduced as part of the starting material where the appropriate surrogate for the B-ring is commercially available or may be prepared using known methods. For example, the use of pyrazine carboxamide, nicotinamide or substituted analogs thereof results in substituted derivatives or analogs of compounds of formula 3a or 6a, which are also compounds of the present invention. Primary and secondary amines are useful for the reductive amination to convert compound 4a to compound 6a as shown in Scheme 2. Examples of useful amines for the reductive amination include but are not limited to phenethylamine, 3-methylbutylamine, propylamine, isopropylamine, benzylamine and isopentylamine.

Compounds prepared by this and other schemes disclosed herein, or known to one of skill in the art may further be converted to the acid addition salt as shown for example, in Scheme 3.

Scheme 3

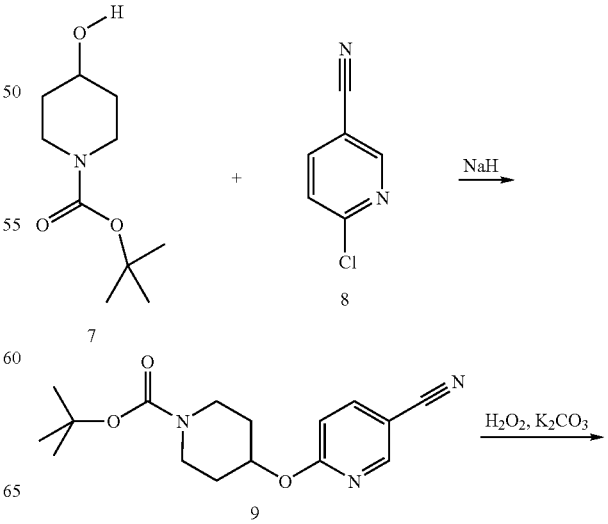

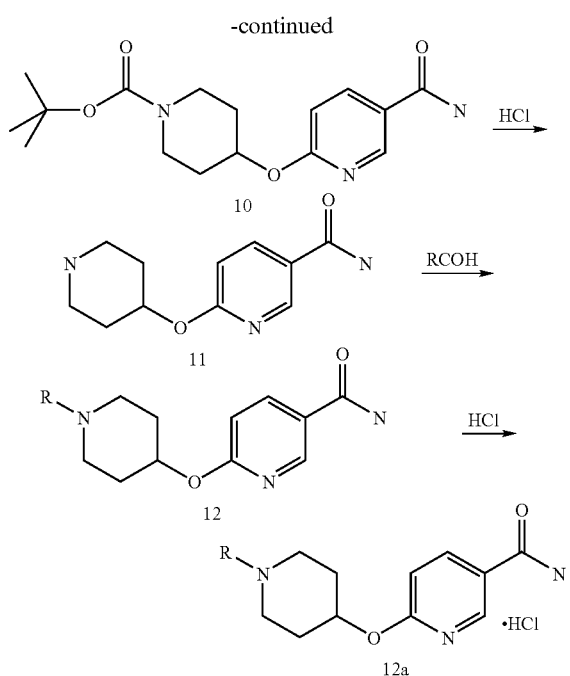

Scheme 3 shows preparation of the hydrochloride salt 12a, a compound of the invention wherein $R^1R^2NH$ is 3-methylbutylamine or other secondary amine group and $R^4$ and $R^5$ are both hydrogen. As shown, the starting material 7 is 4-hydroxy piperidine protected at the nitrogen atom using tertiary butoxycarbonyl anhydride (Boc-anhydride). The Boc-protected piperidinol (7) is reacted with a source of the B-ring such as a halobenzonitrile, or a haloniconitrile (6-chloro-nicotinonitrile (8) shown) or halopyridazino nitrile or carboxamide thereof as desired. The coupling reaction to form the ether linkage (9) is performed in the presence of a base such as sodium hydride or sodium carbonate in a suitable solvent such as DMA, DMF, or DMSO. The nitrile group of the resulting ether (9) is then hydrolyzed to form the primary amide. Hydrolysis of the nitrile is accomplished in the presence of hydrogen peroxide and a base such as sodium carbonate. The resulting amide 10 is hydrolyzed under acidic conditions to afford the deprotected compound 11. Deprotection of the Boc group is best accomplished using HCl, TFA or HF. Procedures for Boc-protection and deprotection are known to one of skill in the art and are described in general Organic chemistry references including *Protecting groups in Organic Synthesis*, 3$^{rd}$ edition, Greene, T. W.; Wuts, P. G. M. Eds., John Wiley and Sons, New York, 1999. Specific procedures may also be found in the experimental section herein. The free piperidinyl NH group of compound 11 may be reacted with an aldehyde having the desired alkyl, alkylaryl, cycloalkyl, alkylcycloalkyl, alkylheterocyclic or other substituent within the scope of the invention to afford the desired N-substituted piperidinyl compound 12.

The compound 12 is dissolved in ethanol and a slight excess (e.g 1.0 to 1.5 molar equivalents based on the number of basic sites) of 1N hydrochloric acid is added at temperatures ranging from about 0° C. to room temperature. The mixture may be allowed to crystallize over time with or without cooling, or may be evaporated to afford the hydrochloride salt, which may be further purified by trituration with a suitable organic solvent such as toluene, hexanes, diethylether or mixtures thereof. Alternatively, anhydrous HCl may be bubbled into a cold solution of compound 12 until the reaction is complete or the solution is saturated, and the mixture worked up as appropriate to afford compound 12a. One of skill in the art is aware of the nuances and the varied techniques for preparing, isolating and purifying acid addition salts, and should achieve comparable results using methods appropriate for the particular substrate without undue experimentation.

A modified protocol for preparing compounds of the invention is provided in Scheme 4 wherein the nucleophilic displacement reaction to form the ether linkage is performed towards the end of the synthesis rather than early on.

Scheme 4

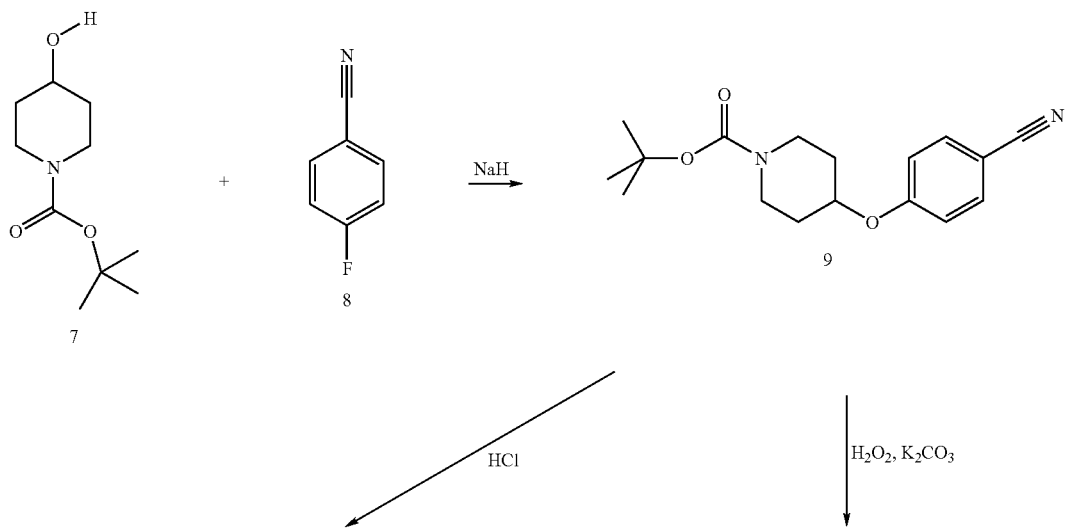

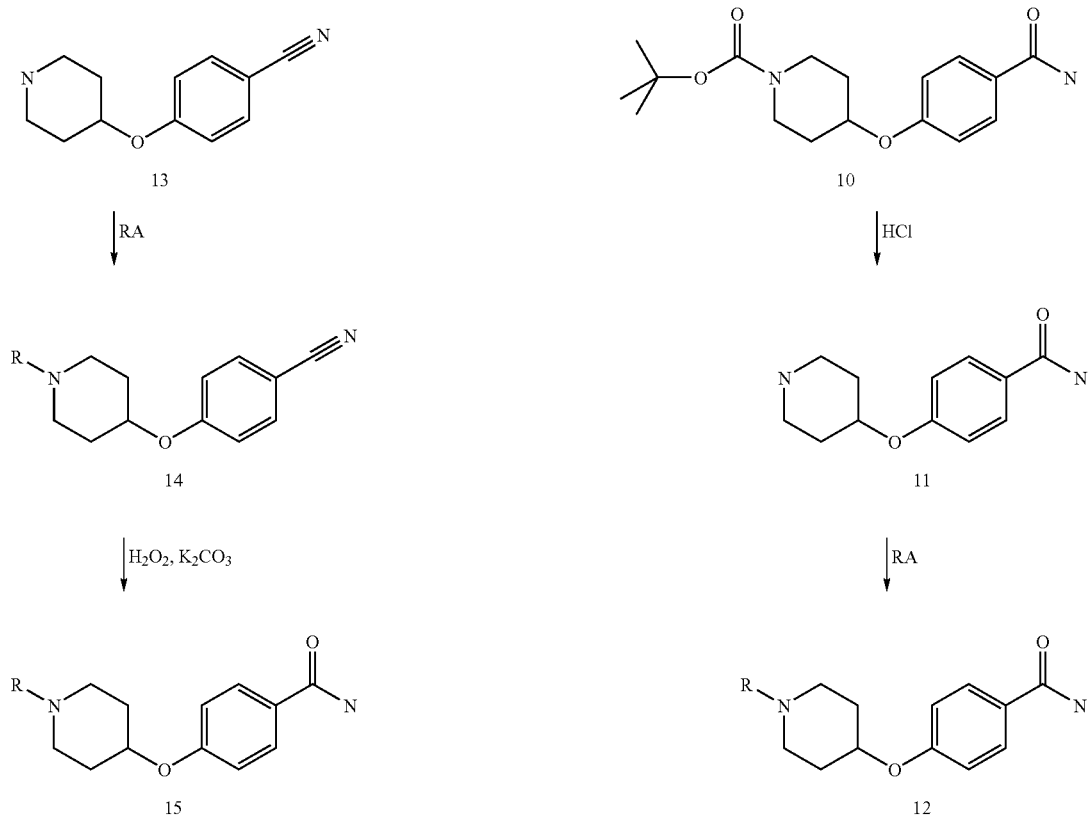

According to Scheme 4, the starting material is an appropriately substituted hydroxypiperidine (7) protected at the nitrogen using Boc anhydride. It may be possible to purchase the Boc-protected hydroxy piperidine. The Boc protected hydroxypiperidine 7 is reacted with a B-ring source such as 4-fluorobenzonitrile to afford the ether linked compound 9. Other B ring sources include for example, phenyl or pyridine carboxamide, benzonitrile or pyridino-nitrile and analogs thereof. Methods of accomplishing the coupling reaction have been disclosed previously. The compound 9 may be hydrolyzed to the amide via the nitrile group, deprotected by removing the Boc group as disclosed previously, and finally reductively aminated to afford a compound of the invention. Alternatively, the ether compound 9 may be deprotected by removing the Boc group to afford the compound 13. The protecting group may be removed by use of hydrochloric acid or trifluoroacetic acid using procedures known to one of skill in the art. One of skill in the art is aware that appropriately substituted analogs of the compound of formula 13 may be prepared by starting with appropriately substituted starting materials or surrogates thereof which may be converted to the desired substituents.

Deprotection of compound 9 to form compound 13 is followed by reductive amination to form the N-substituted piperidinyl compound 14. The N-substituted piperidinyl compound 14 is finally hydrolyzed at the nitrile group to afford compound 15, a compound of the invention.

Compounds of formula I wherein v is 1 may be made following the synthetic scheme described below:

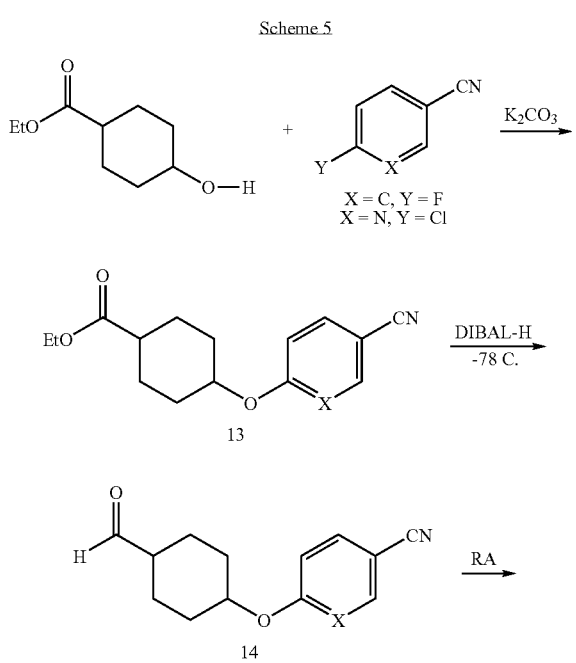

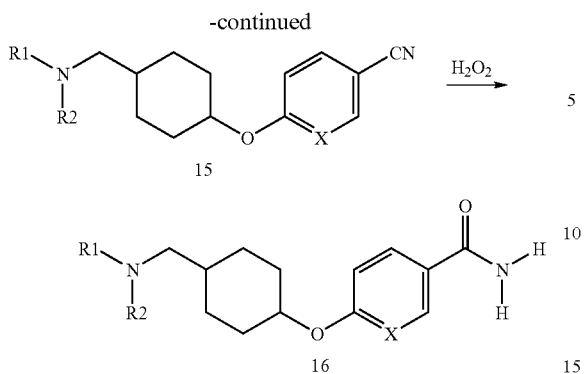

As shown in Scheme 5 4-hydroxy-cyclohexanecarboxylic acid ethyl ester (commercially available from Aldrich Chemical Company, Milwaukee, USA or other fine chemical suppliers) may be reacted with a source of the B-ring such as halobenzonitrile or haloniconitonitrile to form the ether linked product 13. The coupling reaction to form the ether linkage is performed in the presence of a base such as sodium hydride or potassium carbonate in a suitable solvent such as DMA, DMF or DMSO. The carboxylic acid ester is then selectively reduced to give the corresponding aldehyde 14. This reduction is accomplished with hydrides such as for example diisobutylalumnum hydride (DIBAL-H). The aldehyde 14 is then reductively aminated with the desired amino moiety to form the amine 15. The nitrile of the resulting amino precursor is then hydrolyzed to yield a compound of the invention 16.

Yet another protocol for the preparation of compounds of formula I is shown in Scheme 6.

The aldehyde 14 of scheme 5 is reacted with methoxymethyldiphenyl phosphine oxide or methoxymethytriphenyphosphonium chloride in the presence of a strong base such as n-butyl lithium, sec-butyl; lithium or potassium hexamethyldisilane or the like to afford the vinyl methylether 17. The vinylmethyl ether 17 is then hydrolyzed under acidic conditions to afford the higher aldehyde 18. The aldehyde 18 is then converted to the desired compound 20 of formula I as shown and discussed previously.

Method of Using the Invention

As noted above, the compounds of the present invention are useful in blocking the effect of agonists at mu, kappa, and/or delta opioid receptors. As such, the present invention also provides a method for blocking a mu, kappa, delta receptor or receptor combination (heterodimer) thereof in a mammal comprising administering to said mammal a receptor blocking dose of a compound of formula I.

The term "receptor blocking dose", as used herein, means an amount of a compound of formula I necessary to block a mu, kappa, or delta receptor or receptor combination (heterodimer) thereof following administration to a mammal requiring blocking of a mu, kappa, or delta receptor or receptor combination (heterodimer) thereof.

The compounds of formula I or combinations thereof, are effective over a wide dosage range. For example, dosages per day will normally fall within the range of about 0.05 to about 250 mg/kg of body weight. In the treatment of adult humans, the range of about 0.5 to about 100 mg/kg, in single or divided doses, is preferred. However, it will be understood that the amount of the compound actually administered will be determined by a physician in light of the relevant circumstances, including the condition to be treated, the choice of compound to be administered, the age, weight, and response of the individual patient, the severity of the patient's symptoms, and the chosen route of administration. Therefore, the above dosage ranges are not intended to limit the scope of the invention in any way. The compounds may be administered by a variety of routes such as the oral, transdermal, subcutaneous, sublingual, intranasal, intramuscular and intravenous routes.

A variety of physiologic functions have been shown to be subject to or influenced by mu, kappa, or delta receptors or receptor combination (heterodimers) in the brain. As such, the compounds of the present invention are believed to have the ability to treat disorders associated with these receptors or combinations thereof, such as eating disorders, opioid overdose, depression, smoking, alcoholism, sexual dysfunction, shock, stroke, spinal damage and head trauma. As such, the present invention also provides methods of treating the above disorders by blocking the effect of agonists at a mu, kappa, delta receptors or receptor combinations (heterodimer) thereof. The compounds of the present invention have been found to display excellent activity in an opioid receptor binding assay which measures the ability of the compounds to block the mu, kappa, delta or receptor combination (heterodimer) thereof.

GTP-γ-S-Binding Assay

An SPA—based GTP-γ-S assay format was developed based on previous opioid (Emmerson et al., J. Pharm Exp Ther 278, 1121, 1996; Horng et al., Society for Neuroscience Abstracts, 434.6, 2000) and muscarinic (DeLapp et al., JPET 289, 946, 1999) assay formats. Membranes were re-suspended in 20 mM HEPES, 100 mM NaCl, 5 mM $MgCl_2$, 1 mM DTT, and 1 mM EDTA. Fifty (50) mL of GTP-γ-[35S], compound, membrane suspension (20 microgram/well), and wheat germ agglutinin coated SPA beads (1 mg/well) were added to clear bottom 96 well assay plates. GDP (200 mM) was added to the membrane solution prior to addition to the assay plates. Plates were sealed and incubated for four hours at room temperature then placed in a refrigerator overnight to allow the beads to settle. Signal stability at 4° C. was determined to be >60 hours. Plates were warmed to room temperature and counted in a Wallac Microbeta scintillation counter. For antagonist assays, specific agonists were added at the following concentrations: (MOR) DAMGO 1 micromolar, (DOR) DPDPE 30 nM, (KOR) U69593 300 nM. Kb's were determined by Cheng-Prusoff equation (see Cheng and Prusoff, Biochem. Pharmacol. 22, 3099, 1973). Results obtained for a representative sample of compounds of the invention in the GTP-γ-S Binding Assay are shown in table 1 below.

TABLE 1

In Vitro Antagonism GTP-γ-S Binding Assay

| Compound of Example # | $K_b$ (uM) Mu | $K_b$ (uM) Kappa | $K_b$ (uM) Delta |
|---|---|---|---|
| 1 | 0.566 | 0.601 | 0.819 |
| 2 | 0.594 | 0.620 | 0.996 |
| 6 | >1.800 | 0.430 | >7.300 |
| 7 | 1.785 | 1.051 | >7.300 |
| 8 | >1.850 | 0.937 | >7.300 |
| 9 | 1.120 | 0.930 | >7.300 |
| 10 | 0.453 | 0.999 | 1.965 |

Ex-Vivo Receptor Binding

In order to bridge in vitro binding affinity and antagonist potency to in vivo potency and efficacy applicants have developed an ex vivo receptor binding assay in rat brain. This assay measures the difference in association (binding) of a high affinity nonselective opioid receptor radioligand (3H-diprenorphine) in brain tissue isolated from animals receiving vehicle versus compound treatment (less binding of 3H-diprenorphine=greater compound association with opioid receptors). Studies using the ex-vivo receptor binding assay have demonstrated a positive correlation between activity (potency and duration of activity) which also correlates to 24 hour efficacy in dietary induced obese rats.

Methods. An opioid receptor ex vivo binding assay measures 3H-diprenorphine binding (0.1–0.4 nM affinity radioligand for mu, delta and kappa receptors) in rat striatum/nucleus accumbens; a region of the brain that contains a high density of mu, delta and kappa receptors, following oral administration of compounds. Experimentally, a screening dose of 7 mg/kg, p.o. of compound or vehicle is administered to rats. Six hours following compound administration, the animals are sacrificed and the striatum/nucleus accumbens is isolated and homogenized in 10 volumes (weight/volume) binding buffer. The homogenate is then used in a homogenate binding assay using a saturating concentration of 3H-diprenorphine for 30 minutes. The homogenization and assay is performed at 4° C., to minimize compound redistribution in the in vitro binding portion of the assay. Results are reported (Table 2) as specific binding constant Ki in micromolar (uM).

TABLE 2

SPA Binding Affinity assay $K_i$ (uM)

| Compound of Example No. | Mu | Kappa | Delta |
|---|---|---|---|
| 3 | 0.137 | 2.561 | 0.353 |
| 4 | 0.620 | >5.000 | 2.345 |

Formulation

A compound of the invention is preferably presented in the form of a pharmaceutical formulation comprising a pharmaceutically acceptable carrier, diluent or excipient and a compound of the invention. Such compositions will contain from about 0.1 percent by weight to about 90.0 percent by weight of the compound of the invention (Active Ingredient). As such, the present invention also provides pharmaceutical formulations comprising a compound of the invention and a pharmaceutically acceptable carrier, diluent or excipient thereof.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material that acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

For oral administration, the Active Ingredient, a compound of this invention, may be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the Active Ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In order to more fully illustrate the operation of this invention, the following formulation examples are provided.

The examples are illustrative only, and are not intended to limit the scope of the invention. The formulations may employ as Active Ingredient any of the compounds of the present invention.

Formulation 1

Hard gelatin capsules are prepared using the following ingredients:

| Compound | Amount per capsule (mg) | Concentration by weight (%) |
|---|---|---|
| Active Ingredient | 250 | 55 |
| Starch dried | 200 | 43 |
| Magnesium stearate | 10 | 2 |

The above ingredients are mixed and filled into hard gelatin capsules in 460 mg quantities.

Formulation 2

Capsules each containing 20 mg of medicament are made as follows:

| Compound | Amount per capsule (mg) | Concentration by weight (%) |
|---|---|---|
| Active Ingredient | 20 | 10 |
| Starch | 89 | 44.5 |
| Microcrystalline cellulose | 89 | 44.5 |
| Magnesium stearate | 2 | 1 |

The active ingredient, cellulose, starch and magnesium stearate are blended, passed through a No. 45 mesh U.S. sieve and filled into a hard gelatin capsule.

Formulation 3

Capsules each containing 100 mg of active ingredient are made as follows:

| Compound | Amount per capsule (mg) | Concentration by weight (%) |
|---|---|---|
| Active Ingredient | 100 | 30 |
| Polyoxyethylene Sorbitan monooleate | 50 mcg | 0.02 |
| Starch powder | 250 | 69.98 |

The above ingredients are thoroughly mixed and placed in an empty gelatin capsule.

Formulation 4

Tablets each containing 10 mg of active ingredient are prepared as follows:

| Compound | Amount per capsule (mg) | Concentration by weight (%) |
|---|---|---|
| Active Ingredient | 10 | 10 |
| Starch | 45 | 45 |
| Microcrystalline cellulose | 35 | 35 |
| Polyvinylpyrrolidone (as 10% solution in water) | 4 | 4 |
| Sodium carboxymethyl starch | 4.5 | 4.5 |
| Magnesium stearate | 0.5 | 0.5 |
| talc | 1 | 1 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50–60° C. and passed through a No. 18 mesh U.S. sieve. The sodium carboxymethyl starch, magnesium stearate and talc, previously passed through a No. 60 mesh U.S. sieve, are then added to the granules, which after mixing, is compressed on a tablet machine to yield a tablet weighing 100 mg.

Formulation 5

A tablet formula may be prepared using the ingredients below:

| Compound | Amount per capsule (mg) | Percent by weight (%) |
|---|---|---|
| Active Ingredient | 250 | 38 |
| Cellulose microcrystalline | 400 | 60 |
| Silicon dioxide fumed | 10 | 1.5 |
| Stearic acid | 5 | 0.5 |

The components are blended and compressed to form tablets each weighing 665 mg.

Formulation 6

Suspensions each containing 5 mg of medicament per 5 mL dose are made as follows:

| Compound | Amount per 5 mL suspension (ml) |
|---|---|
| Active Ingredient | 5 |
| Sodium carboxymethyl cellulose | 50 |
| Syrup | 1.25 |
| Benzoic acid solution | 0.10 |
| Flavor | q.v. |
| Color | q.v. |
| Water | q.s. to 5 mL |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

| Compound | Concentration by weight (percent) |
| --- | --- |
| Active Ingredient | 0.25 |
| Ethanol | 29.75 |
| Propellant 22 (chlorodifluoromethane) | 70.0 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

EXAMPLES

Example 1

±6-{4-[2-(Tetrahydro-pyran-4-yl)-ethylamino]-cyclohexyloxy}-nicotinamide,

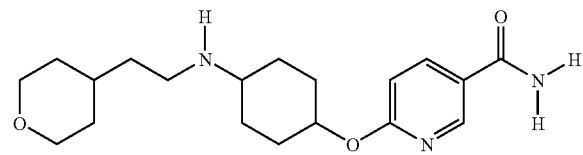

Step 1

Preparation of 3,3-Dimethyl-1,5-dioxa-spiro[5.5]undecan-9-ol

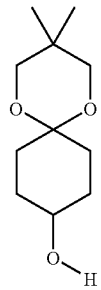

Combine 3,3-dimethyl-1,5-dioxa-spiro[5.5]undecan-9-one (Aldrich, 750 mg, 3.78 mmol) with polymer-supported borohydride (Aldrich, 3026 mg, 7.56 mmol) in methanol (30 mL). Shake by rotation the resulting mixture overnight. Filter the reaction mixture and concentrate the filtrate. Wash the residue with hydrochloric acid 0.1M and extract with EtOAc. Dry the organic layer over sodium sulfate, filter and concentrate.

Step 2

Preparation of 6-(3,3-Dimethyl-1,5-dioxa-spiro[5.5]undec-9-yloxy)-nicotinonitrile

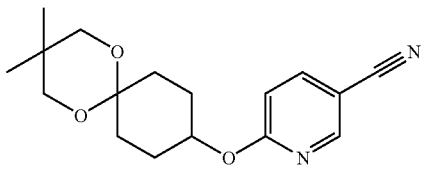

Add dropwise a solution of 3,3-dimethyl-1,5-dioxa-spiro[5.5]undecan-9-ol, (1445 mg, 7.22 mmol) in DMF (2.1 mL) to a suspension of sodium hydride (433 mg, 10.82 mmol) in DMF (8.6 mL). Let the reaction mixture stir at room temperature for 1 h, then heat while stirring at 50° C. for 20 min. Add dropwise a solution of 6-chloro-nicotinonitrile (1200 mg, 8.66 mmol) in DMF (4.5 mL). Continue the heating at 60° C. and stirring overnight. Concentrate the reaction mixture to remove DMF. Wash the residue with water (15 mL) and extract with EtOAc/hexanes (20 mL). Dry the organic layer over sodium sulfate, filter and concentrate. Purify the residue by flash chromatography (eluent $CH_2Cl_2$/hexanes 2/1) to give 2000 mg (92% yield) of the title compound.

Step 3

Preparation of 6-(4-Oxo-cyclohexyloxy)-nicotinonitrile

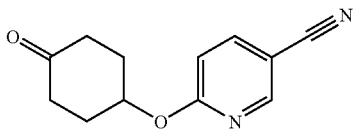

Combine hydrochloric acid (1.0M aq., 20 mL) with a solution of 6-(3,3-dimethyl-1,5-dioxa-spiro[5.5]undec-9-yloxy)-nicotinonitrile (2000 mg, 6.61 mmol) in acetone (25 mL). Stir at room temperature for 2 h then at 40–50° C. for 1 h. Concentrate the reaction mixture. Partition the residue between EtOAc/hex (25 mL) and $K_2CO_3$ (aq. sat. 20 mL). Wash the organic layer with water, brine, and dry it over sodium sulfate, filter and concentrate. Triturate the residue with EtOAc/hexanes (1/4) to provide a white solid which is further purified by flash chromatography (EtOAc/Hexanes 1/4) to give 1010 mg (71% yield) as a white solid.

Step 4

Preparation of 6-{4-[2-(Tetrahydro-pyran-4-yl)-ethylamino]-cyclohexyloxy}-nicotinonitrile, NE4-A05445-035

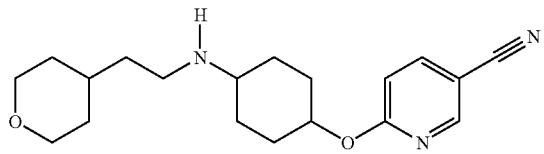

Combine the previously obtained 6-(4-oxo-cyclohexyloxy)-nicotinonitrile, (200 mg, 0.925 mmol), 2-(tetrahydro-pyran-4-yl)-ethylamine (Aldrich, 125 mg, 0.971 mmol) and a scoop of molecules sieves 3 Å in methanol (4 mL). Let the reaction mixture stir overnight, and then add sodium borohydride (70 mg, 1.85 mmol). Continue the stirring overnight. Purify the reaction mixture by loading onto an SCX column, washing with methanol and eluting with ammonia/methanol (2.0M). Purify the residue by two flash chromatographies (40/1 CH$_2$Cl$_2$/ammonia in methanol) to provide 199 mg (65%) of the title compound as pale yellow oil.

Step 5

Combine the previously obtained 6-{4-[2-(tetrahydro-pyran-4-yl)-ethylamino]-cyclohexyloxy}-nicotinonitrile (199 mg, 0.604 mmol) and potassium carbonate in DMSO (4 mL). Cool the reaction mixture to 0° C., and then add hydrogen peroxide (0.181 mL) dropwise. Let the reaction mixture stir at room temperature for 3 h. Pour the mixture onto water. Filter the precipitate and redissolved in methanol. Concentrate and purify through an SCX column to provide the title compound. Mass spectrum (ion spray): m/z=348.3 (M+1); $^1$H NMR (CDCl$_3$): 8.62 (s, 1H), 8.04 (m, 1H), 6.75 (m, 1H), 6.01 (bs, 2H), 5.32 (bs, 1H), 5.07 (m, 1H), 3.97 (dd, J=11.0 and 4.0 Hz, 2H), 3.40 (t, J=11.4 Hz, 2H), 2.73–2.54 (m, 3H), 2.21–2.03 (m, 3H), 1.79–1.28 (m, 12H).

Example 2

±6-[4-(3-Methyl-butylamino)-cyclohexyloxy]-nicotinamide

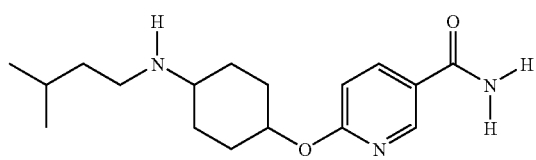

Using a method similar to example 1, gives the title compound (199 mg, 96%). Mass spectrum (ion spray): m/z=306.3 (M+1); $^1$H NMR (CDCl$_3$): 8.66 (s, 1H), 8.13–8.10 (m, 1H), 7.96 (bs, 1H), 7.39 (bs, 1H), 6.81 (m, 1H), 5.17 (s, 1H), 5.00 (m, 1H), 2.49 (m, 3H), 2.06–1.14 (m, 14H), 0.88 (t, J=6.6 Hz, 6H).

Example 3

±6-[4-(2-Thiophen-2-yl-ethylamino)-cyclohexyloxy]-nicotinamide

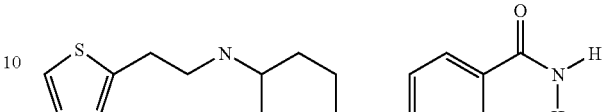

Using a method similar to example 1, gives the title compound (203 mg, 87%). Mass spectrum (ion spray): m/z=346.1 (M+1); $^1$H NMR (CDCl$_3$): 8.61 (s, 1H), 8.05–8.00 (m, 1H), 7.17 (m, 1H), 6.96 (m, 1H), 6.87 (s, 1H), 6.98–6.95 (m, 1H), 6.03 (bs, 2H), 5.31–5.04 (m, 1H), 3.07–2.96 (m, 4H), 2.67–2.55 (m, 1H), 2.20–2.00 (m, 3H), 1.78–1.26 (m, 6H).

Example 4

4-[4-(3-Phenyl-propylamino)-cyclohexyloxy]-benzamide

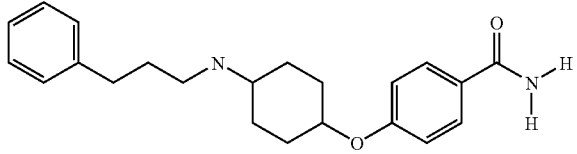

Step 1

4-(3,3-Dimethyl-1,5-dioxa-spiro[5.5]undec-9-yloxy)-benzonitrile

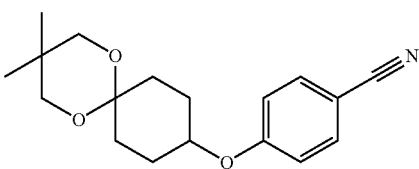

Add dropwise a solution of 3,3-dimethyl-1,5-dioxa-spiro [5.5]undecan-9-ol, (NE4-A05445-029, 1377 mg, 6.88 mmol) in DMF (2.0 mL) to a suspension of sodium hydride (412 mg, 10.32 mmol) in DMF (8.0 mL). Let the reaction mixture stir at room temperature for 1 h, then heat while stirring at 50° C. for 20 minutes (min). Add dropwise a solution of 4-fluoro-benzonitrile (1000 mg, 8.26 mmol) in DMF (4.2 mL). Continue the heating at 60° C. and stirring for 2 hours (h). Concentrate the reaction mixture to remove DMF. Wash the residue with water (15 mL) and extract with EtOAc/hexanes (20 mL). Dry the organic layer over sodium sulfate, filter and concentrate. Purify the residue by flash chromatography (eluent CH$_2$Cl$_2$/hexanes 2/1) to give xxx mg (xx % yield) of the title compound.

Step 2

4-(4-Oxo-cyclohexyloxy)-benzonitrile

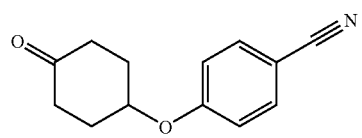

Combine hydrochloric acid (1.0M aq., 20 mL) with a solution of in acetone (25 mL). Stir at room temperature for 2 hours then at 40–50° C. for 1 h. Concentrate the reaction mixture. Partition the residue between EtOAc/hex (25 mL) and $K_2CO_3$ (aq. sat. 20 mL). Wash the organic layer with water, brine. Dry the organic layer over sodium sulfate, filter and concentrate. Triturate the residue with EtOAc/hexanes (1/4) to provide a white solid which is further purified by flash chromatography (EtOAc/Hexanes 1/4) to give mg (% yield) as a white solid.

Step 3

4-(4-Oxo-cyclohexyloxy)-benzamide

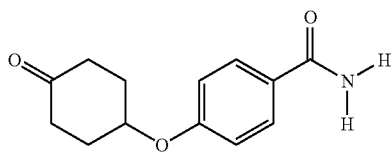

Combine 4-(4-oxo-cyclohexyloxy)-benzonitrile previously obtained (100 mg, 0.464 mmol), $K_2CO_3$ (32 mg, 0.232 mmol) in DMSO (23 mL). Cool the reaction mixture to 0° C. and add hydrogen peroxide (0.139 mL). Let stir the reaction mixture for 4 h at room temperature. Quench the reaction mixture with water (15 mL). Extract with EtOAc/hex 2/1 (3×20 mL). Dried over sodium sulfate, filter and concentrate. Purify the residue by flash chromatography (20/1 $CH_2Cl_2$/ammonia in methanol 2.0M) to provide the title compound (40 mg, 37%).

Step 4

Combine 4-(4-oxo-cyclohexyloxy)-benzamide (20 mg, 0.085 mmol), 3-phenyl-propylamine (11 mg, 0.085 mmol), triacetoxyborohydride (23 mg, 0.111 mmol) and acetic acid (5 µL, 0.085 mmol) in $CH_2Cl_2$ (1 mL). Let stir overnight. Purify by SCX column (ammonia in methanol 2.0M). Triturate the residue with EtOAc/hexanes 1/1 to provide a white powder (25 mg, 86%).

Example 5

Trans-6-(4-Benzylamino-cyclohexyloxy)-nicotinamide

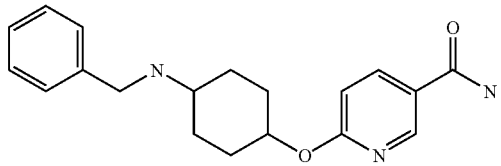

Step 1

4-Benzylamino-cyclohexanol

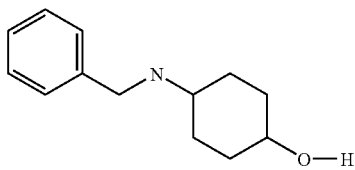

Combine trans-4-amino-cyclohexanol (2.0 g, 17.4 mmol) in methanol (75 mL) in a sealed tube then add benzaldehyde (1.85 mL, 18.23 mmol). Heat the reaction mixture at 70° C. while stirring for 2 h. Then let the reaction cool down and add sodium borohydride (2.46 g, 65.1 mmol) in portions. Stir overnight. Evaporate the solvent till ⅓ of the original volume. Partition the reaction mixture between EtOAc (50 mL) and water (40 mL). Reextract the aqueous layer with EtOAc (20 mL). Combine the organic layers and dry over sodium sulfate. Filter and concentrate to provide the title compound (3.5 g) that will be use directly in the next step.

Step 2

6-(4-Benzylamino-cyclohexyloxy)-nicotinonitrile

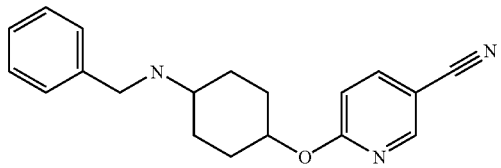

Add dropwise a solution of 4-benzylamino-cyclohexanol (675 mg, 3.28 mmol) in DMF (2 mL) to a suspension of NaH (196 mg, 4.92 mmol) in DMF (3 mL). Stir at room temperature for 45 min then at 50° C. for additional 40 min. Add a solution of 6-chloro-nicotinonitrile (500 mg, 3.61 mmol) in DMF (1.8 mL) dropwise and stir overnight at 60° C. Cool down the reaction mixture and evaporate the solvent. Wash the residue with water (10) and extract with EtOAc/hex (2/1, 15 mL). Combine the organic layers and dry over sodium sulfate. Filter and concentrate. Purify the resulting residue through an SCX column. Further purified by chromatography [$CH_2Cl_2/NH_3$ (2.0M in methanol) 20/1] to provide the title compound (890 mg, 88%).

Step 3

Add K$_2$CO$_3$ (200 mg, 1.44 mmol) to a solution of 6-(4-benzylamino-cyclohexyloxy)-nicotinonitrile (890 mg, 2.89 mmol) in DMSO (25 mL). Cool the reaction to 0° C. and add hydrogen peroxide (0.87 mL). Stir the resulting reaction mixture at room temperature for 2 h. Then quench the reaction mixture with water (25 mL) and extract with EtOAc (30 mL). Dried over sodium sulfate, filter and concentrate. Further purify the residue by SCX chromatography to provide the title compound (700 mg, 74%). Mass spectrum (ion spray): m/z=326.0 (M+1); $^1$H NMR (CDCl$_3$): 8.61 (s, 1H), 8.04 (m, 1H), 7.36 (m, 5H), 6.74 (d, J=8.8 Hz, 1H), 5.10 (m, 1H), 3.87 (s, 2H), 2.64 (m, 1H), 2.22–2.07 (m, 4H), 1.58–1.33 (m, 4H).

Example 6

6-(1-Pyridin-2-ylmethyl-piperidin-4-yloxy)-nicotinamide

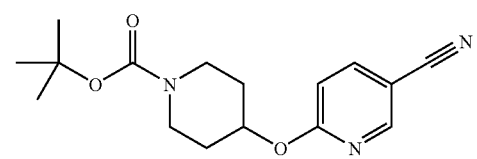

Step 1

4-(5-Cyano-pyridin-2-yloxy)-piperidine-1-carboxylic acid tert-butyl ester

Add dropwise a solution of 4-hydroxy-piperidine-1-carboxylic acid tert-butyl ester (1210 mg, 6.01 mmol) in DMF (1.8 mL) to a suspension of NaH (360 mg, 9.02 mmol) in DMF (7.2 mL). Stir at room temperature for 45 min then at 50° C. for additional 40 min. Add a solution of 6-chloro-nicotinonitrile (1000 mg, 7.22 mmol) in DMF (3.6 mL) dropwise and stir overnight at 60° C. Cool down the reaction mixture and evaporate the solvent. Wash the residue with water (10) and extract with EtOAc/hex (2/1, 15 mL). Combine the organic layers and dry over sodium sulfate. Filter and concentrate. Purify the resulting residue through an SCX column. Further purified by chromatography [CH$_2$Cl$_2$/NH$_3$ (2.0M in methanol) 20/1] to provide the title compound (1.73 g, 94%).

Step 2

4-(5-Carbamoyl-pyridin-2-yloxy)-piperidine-1-carboxylic acid tert-butyl ester

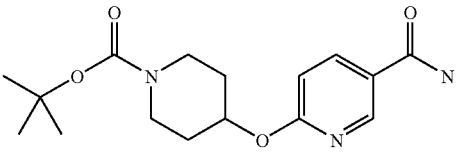

Combine a solution of 4-(5-cyano-pyridin-2-yloxy)-piperidine-1-carboxylic acid tert-butyl ester (1630 mg, 5.38 mmol) in DMSO (50 mL) with potassium carbonate (371 mg, 2.69 mmol). Cool the solution to 0° C. and add slowly hydrogen peroxide (1.61 mL). After 10 min, stir the reaction mixture at room temperature for 2 h. Add water (25 mL) and extract twice with CH$_2$Cl$_2$ (30 mL). Dry the organic layer over sodium sulfate, filter and concentrate to provide the title compound (1669 mg, 97%) as a white solid.

Step 3

6-(Piperidin-4-yloxy)-nicotinamide hydrochloride

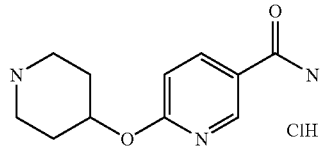

Combine 4-(5-carbamoyl-pyridin-2-yloxy)-piperidine-1-carboxylic acid tert-butyl ester (1559 mg, 4.85 mmol) in tetrahydrofuran (25 mL) with hydrochloric acid (4.0 M in dioxane, 15 mL). Stir the resulting reaction mixture for 48 h. Filter the white precipitate washing with EtOAc (10 mL). Redissolve the white solid in methanol and concentrate to provide the title compound (1195 mg, 89%).

Step 4

Combine 6-(piperidin-4-yloxy)-nicotinamide (100 mg, 0.45 mmol) with sodium triacetoxy-borohydride (124 mg, 0.59 mmol) and pyridine-2-carbaldehyde (43 μL, 045 mmol) in CH$_2$Cl$_2$ (1.5 mL). Stir the reaction mixture for 3 h. Then, dilute the reaction mixture with CH$_2$Cl$_2$ (5 mL) and washed with NaOH (1M aq, 5 mL). Dry the organic layer over sodium sulfate, filter and concentrate. Purify the residue through an SCX chromatography to provide the title compound (83 mg, 59%). Mass spectrum (ion spray): m/z=313.1 (M+1); $^1$H NMR (DMSO-d$_6$): 8.67 (ad, J=2.2 Hz, 1H), 8.50 (m, 1H), 8.12 (dd, J=2.6 and 8.8 Hz, 1H), 7.98 (bs, 1H), 7.80–7.76 (m, 1H), 7.47 (d, J=7.9 Hz, 1H), 7.41 (bs, 1H), 7.29–7.26 (m, 1H), 6.84 (d, J=8.8 Hz, 1H), 5.10 (m, 1H), 3.63 (m, 2H), 2.77–2.74 (m, 2H), 2.35–2.30 (m, 2H), 1.99 (bs, 2H), 1.75–1.69 (m, 2H).

Example 7

6-(1-Cyclopropylmethyl-piperidin-4-yloxy)-nicotinamide

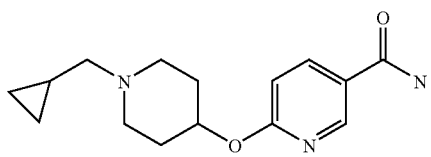

Using a method similar to example 6, gives the title compound (89 mg, 72%). Mass spectrum (ion spray): m/z=276.1 (M+1); $^1$H NMR (DMSO-d$_6$): 8.66 (m, 1H), 8.12 (app. dd, J=2.2 and 8.3 Hz, 1H), 7.97 (bs, 1H), 7.40 (bs, 1H), 6.84 (app. d, J=8.3 Hz, 1H), 5.08–5.03 (m, 1H), 2.82 (bs, 2H), 2.52 (s, 1H), 2.27–2.20 (m, 3H), 1.99 (m, 2H), 1.72 (m, 2H), 0.86–0.83 (m, 1H), 0.50–0.45 (m, 2H), 0.10–0.07 (m, 2H).

Example 8

6-[1-(1H-Indol-2-ylmethyl)-piperidin-4-yloxy]-nicotinamide

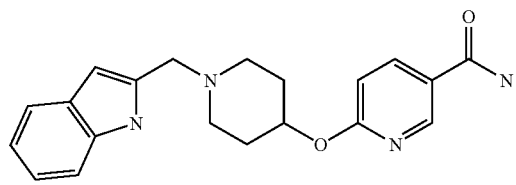

Using a method similar to example 6, gives the title compound (110 mg, 70%). Mass spectrum (ion spray): m/z=351.1 (M+1).

Example 9

4-(1-Benzyl-piperidin-4-yloxy)-benzamide

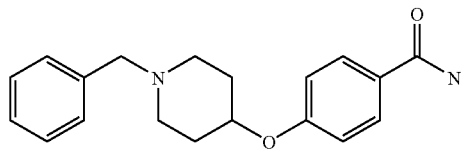

Step 1

4-(4-Cyano-phenoxy)-piperidine-1-carboxylic acid tert-butyl ester

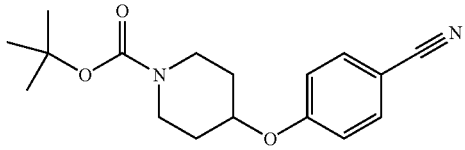

Add a solution of N-Boc-4-hydroxypiperidine (3.0 g, 14.9 mmol) in DMF (5 mL) to a suspension of sodium hydride (894 mg, 22.4 mmol) in DMF (17 mL). Stir the reaction mixture while heating at 50° C. for 45 min. Then add a solution of 4-fluoro-benzonitrile (2.16 g, 17.9 mmol) in DMF (5 mL). Stir and heat at 50° C. for 2 h. Let cool to room temperature and quench with water (0.5 mL). Evaporate DMF. Redissolved the resulting residue in EtOAc/hexanes (2/1, 20 mL) and wash with water (3×15 mL). Dry the organic layer over magnesium sulfate, filter and concentrate. Purify by chromatography (EtOAc/hexanes 20% and EtOAc/hexanes 10%) to yield the title compound (2.32 g, 52%).

Step 2

4-(Piperidin-4-yloxy)-benzonitrile hydrochloride

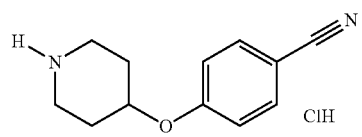

Add dropwise acetyl chloride (2.5 mL) to methanol (5.0 mL) at 0° C. Stir the resulting solution at 0° C. for 90 min. Then add a solution of 4-(4-cyano-phenoxy)-piperidine-1-carboxylic acid tert-butyl ester (284 mg, 0.94 mmol) in methanol. Stir the resulting mixture for 3 h. Evaporate the solvent and triturate with diethyl ether to provide the title compound (216 mg, 96%).

Step 3

4-(1-Benzyl-piperidin-4-yloxy)-benzonitrile

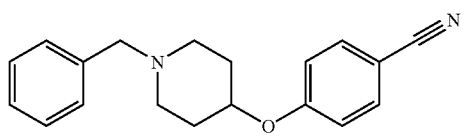

Combine 4-(piperidin-4-yloxy)-benzonitrile hydrochloride (64 mg, 0.268 mmol), benzaldehyde (55 μL, 0.536 mmol) and sodium triacetoxy borohydride (85 mg, 0.402 mmol) in CH$_2$Cl$_2$ (3 mL). Stir at room temperature overnight. Dilute the reaction mixture with CH$_2$Cl$_2$ (3 mL) and wash with NaOH (1M aq. 5 mL). Separate the organic layer and place it in an SCX column, eluting with ammonia (2.0M in methanol) to provide the title compound (74 mg, 95%).

Step 4

Combine 4-(1-benzyl-piperidin-4-yloxy)-benzonitrile (74 mg, 0.25 mmol), DMSO (2.5 mL) and powdered potassium carbonate (18 mg, 0.13 mmol). Cool the resulting mixture to 0° C. and add hydrogen peroxide (76 μL). After addition, stir the mixture at room temperature for 1 h. Quench the reaction mixture with water (2 mL). Filter the precipitate formed rinsing with diethyl ether to give the title compound (57 mg, 73%). Mass spectrum (ion spray): m/z=311.1 (M+1); $^1$H NMR (CDCl$_3$): 7.79 (ad, J=8.6 Hz, 3H), 7.32–7.21 (m, 5H), 7.14 (bs, 1H), 6.95 (d, J=8.6 Hz, 2H), 4.49–4.42 (m, 1H), 3.31 (s, 2H), 2.69–2.62 (m, 2H), 2.27–2.19 (m, 2H), 1.96–1.89 (m, 2H), 1.66–1.56 (m, 2H).

Example 10

4-[1-(3-Phenyl-propyl)-piperidin-4-yloxy]-benzamide

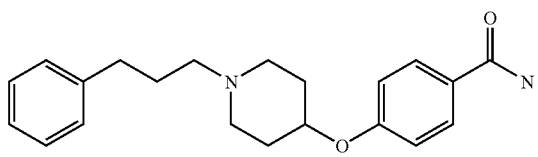

Step 1

4-(4-Carbamoyl-phenoxy)-piperidine-1-carboxylic acid tert-butyl ester

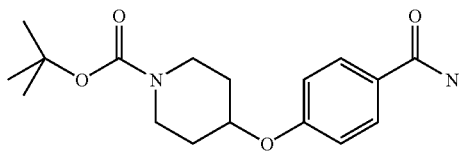

Combine 4-(4-cyano-phenoxy)-piperidine-1-carboxylic acid tert-butyl ester Example 9, step 1, 215 mg, 0.71 mmol) and potassium carbonate (49 mg, 0.36 mmol) in DMSO (35 mL) at 0° C. Then add dropwise hydrogen peroxide (213 μL). Then stir at room temperature for 1 h. Quench the reaction with water (10 mL) and extract with EtOAc/hexanes (2/1, 3×20 mL). Combine the organic layers, dry over magnesium sulfate, filter and concentrate to give the title compound.

Step 2

4-(Piperidin-4-yloxy)-benzamide hydrochloride

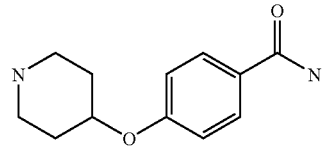

Add hydrochloric acid (4M in dioxane, 3 mL) dropwise to a solution of 4-(4-carbamoyl-phenoxy)-piperidine-1-carboxylic acid tert-butyl ester (228 mg, 0.711 mmol) in THF (2 mL). Stir at room temperature for 7 hours (h). Filter the solids and dry under reduced pressure to give the title compound (180 mg, 99%) as hydrochloride.

Step 3

Combine 4-(piperidin-4-yloxy)-benzamide hydrochloride (102 mg, 0.397 mmol), 3-phenyl-propionaldehyde (106 μL, 0.796 mmol) and triacetoxy-borohydride (127 mg, 0.597 mmol) in CH$_2$Cl$_2$ (3 mL). Stir the reaction mixture at room temperature overnight. Dilute the reaction mixture with CH$_2$Cl$_2$ (3 mL) and wash with sodium hydroxide (1N, aq. 5 mL). Separate the organic layer and placed onto an SCX column directly eluting with ammonia (2.0 in methanol). The resulting residue was triturated with CH$_2$Cl$_2$ and diethyl ether to provide the title compound (63 mg, 47%) as a white solid. mass spectrum (ion spray): m/z=339.1 (M+1); $^1$H NMR (CDCl$_3$): 7.79 (ad, J=9.0 Hz, 3H), 7.28–7.12 (m, 6H), 6.95 (d, J=9.0 Hz, 2H), 4.74–4.40 (m, 1H), 2.70–2.63 (bm, 2H), 2.56 (t, J=7.6 Hz, 2H), 2.31–2.25 (bm, 2H), 2.22–2.15 (bm, 2H), 1.96–1.89 (bm, 2H), 1.71 (pentet, J=7.3 Hz, 2H), 1.63–1.56 (m, 2H).

We claim:

1. A compound selected from the group consisting of:
   6-{4-[2-(tetrahydro-pyran-4-yl)-ethylamino]-cyclohexyloxy}-nicotinamide,

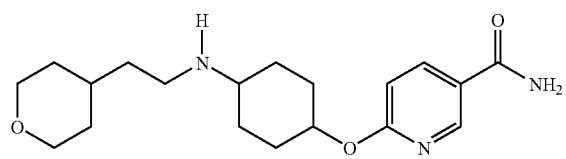

6-[4-(3-Methyl-butylamino)-cyclohexyloxy]-nicotinamide,

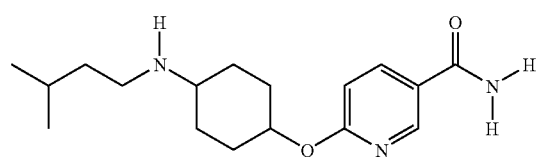

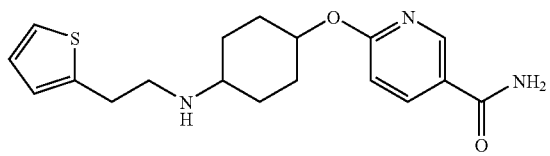

6-[4-(2-Thiophen-2-yl-ethylamino)-cyclohexyloxy]-nicotinamide

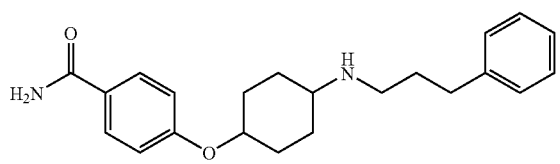

4-[4-(3-Phenyl-propylamino)-cyclohexyloxy]-benzamide
Trans-6-(4-Benzylamino-cyclohexyloxy)-nicotinamide,

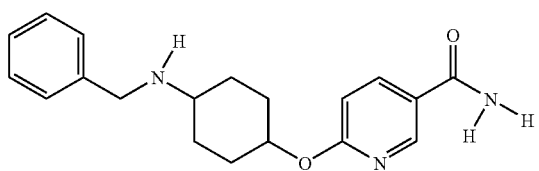

6-(1-Pyridin-2-ylmethyl-piperidin-4-yloxy)-nicotinamide

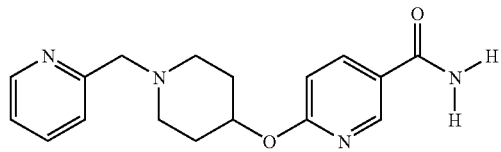

6-(1-Cyclopropylmethyl-piperidin-4-yloxy)-nicotinamide

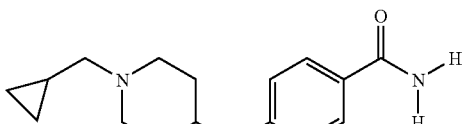

6-[1-(1H-Indol-2-ylmethyl)-piperidin-4-yloxy]-nicotinamide

4-[1-(3-Phenyl-propyl)-piperidin-4-yloxy]-benzamide and a pharmaceutically acceptable salt.

2. A compound according to claim 1 wherein the pharmaceutically acceptable salt is the hydrochloric acid salt, the methanesulfonic acid salt, hydrobromide salt, the bisulfate salt or tartaric acid salt.

3. A pharmaceutical composition comprising a therapeutically effective amount of a compound according to claim 1 in association with a carrier, diluent and/or excipient.

* * * * *